US011649282B2

(12) United States Patent
Jang et al.

(10) Patent No.: US 11,649,282 B2
(45) Date of Patent: May 16, 2023

(54) IMMUNOCYTES EXPRESSING A CHIMERIC ANTIGEN RECEPTOR BINDING TO CANCER CELLS AND TNF-RELATED APOPTOSIS-INDUCING LIGAND (TRAIL)

(71) Applicants: KOREA INSTITUTE OF SCIENCE AND TECHNOLOGY, Seoul (KR); THE ASAN FOUNDATION, Seoul (KR); UNIVERSITY OF ULSAN FOUNDATION FOR INDUSTRY COOPERATION, Ulsan (KR)

(72) Inventors: Mihue Jang, Seoul (KR); Eunsung Jun, Namyangju-si (KR); Anna Ju, Seoul (KR)

(73) Assignees: KOREA INSTITUTE OF SCIENCE AND TECHNOLOGY, Seoul (KR); THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 185 days.

(21) Appl. No.: 16/771,918

(22) PCT Filed: Mar. 10, 2020

(86) PCT No.: PCT/KR2020/003321

§ 371 (c)(1),
(2) Date: Jun. 11, 2020

(87) PCT Pub. No.: WO2020/189942

PCT Pub. Date: Sep. 24, 2020

(65) Prior Publication Data

US 2021/0371515 A1 Dec. 2, 2021

(30) Foreign Application Priority Data

Mar. 15, 2019 (KR) ........................ 10-2019-0029845
Sep. 30, 2019 (KR) ........................ 10-2019-0120852

(51) Int. Cl.

| | |
|---|---|
| ***C07K 16/28*** | (2006.01) |
| ***A61K 35/17*** | (2015.01) |
| ***C07K 14/705*** | (2006.01) |
| ***C12N 15/86*** | (2006.01) |
| ***A61P 35/00*** | (2006.01) |
| ***C07K 14/725*** | (2006.01) |
| ***C12N 5/0783*** | (2010.01) |
| *A61K 38/00* | (2006.01) |
| *A61K 39/00* | (2006.01) |

(52) U.S. Cl.

CPC .............. *C07K 16/28* (2013.01); *A61K 35/17* (2013.01); *A61P 35/00* (2018.01); *C07K 14/7051* (2013.01); *C07K 14/70575* (2013.01); *C07K 14/70578* (2013.01); *C12N 5/0646* (2013.01); *C12N 15/86* (2013.01); *A61K 38/00* (2013.01); *A61K 2039/505* (2013.01); *A61K 2039/5154* (2013.01); *A61K 2039/5156* (2013.01); *C07K 2317/622* (2013.01); *C07K 2317/73* (2013.01); *C07K 2317/76* (2013.01); *C07K 2319/02* (2013.01); *C07K 2319/30* (2013.01); *C07K 2319/33* (2013.01); *C12N 2510/00* (2013.01); *C12N 2740/15043* (2013.01)

(58) Field of Classification Search

CPC ................ C07K 16/28; C07K 14/7051; C07K 14/70575; C07K 14/70578; C07K 2317/622; C07K 2317/73; C07K 2317/76; C07K 2319/02; C07K 2319/30; C07K 2319/33; A61K 35/17; A61K 38/00; A61K 2039/505; A61K 2039/5154; A61K 2039/5156; A61P 35/00; C12N 5/0646; C12N 5/86; C12N 2510/00; C12N 2740/15043

See application file for complete search history.

(56) References Cited

U.S. PATENT DOCUMENTS

2018/0161371 A1 6/2018 O'Dwyer

FOREIGN PATENT DOCUMENTS

| | | | | |
|---|---|---|---|---|
| KR | 10-2018-0028530 A | 3/2018 | | |
| WO | WO-2016097231 A2 * | 6/2016 | ............ | A61K 35/17 |
| WO | WO 2017/017184 A1 | 2/2017 | | |
| WO | WO 2018/104554 A1 | 6/2018 | | |

OTHER PUBLICATIONS

Zhang E and Xu H (2017). J Hematol Oncol. 2017; 10 (11 pages), (doi: 10.1186/s13045-016-0379-6).*

Sengsayadeth S, et al. (2022) eJHaem. 3(Suppl.1):6-10. (DOI:10.1002/jha2.338).* https://www.cancer.gov/about-cancer/treatment/research/car-t-cells (accessed from the internet Sep. 7, 2022).*

(Continued)

*Primary Examiner* — Robert S Landsman

(74) *Attorney, Agent, or Firm* — Birch, Stewart, Kolasch & Birch, LLP

(57) ABSTRACT

Provided are a genetically modified immunocyte expressing a chimeric antigen receptor (CAR) comprising an antigen binding domain specifically binding to cancer cells and/or expressing TRAIL, a composition for preventing or treating cancer, the composition comprising the immunocytes, a cell therapeutic agent, a method of providing information for cancer diagnosis, and a method of preparing the genetically modified immunocyte.

12 Claims, 12 Drawing Sheets

Specification includes a Sequence Listing.

(56) References Cited

OTHER PUBLICATIONS https://www.biocompare.com/pfu/110447/soids/335834/Antibodies/TRAIL (accessed from the internet Sep. 7, 2022).*
https://www.biocompare.com/pfu/110447/soids/277051/Antibodies/FOLR1 (accessed from the internet Sep. 7, 2022).*
Cartellieri et al.. "Chimeric Antigen Receptor-Engineered T Cells for Immunotherapy of Cancer," Journal of Biomedicine and Biotechnology (2010), vol. 2010, Article ID 956304, pp. 1-13.
International Search Report dated Jun. 18, 2020, in PCT/KR2020/003321.
Kim et al., "Folate receptor (FOLR1) targeted chimeric antigen receptor (CAR) T Cells for the treatment of gastric cancer," PLOS One (2018), vol. 13, No. 6, e0198347, pp. 1-20.

* cited by examiner

IMMUNOCYTES EXPRESSING A CHIMERIC ANTIGEN RECEPTOR BINDING TO CANCER CELLS AND TNF-RELATED APOPTOSIS-INDUCING LIGAND (TRAIL)

CROSS REFERENCE TO RELATED APPLICATIONS

This application is the National Phase of PCT International Application No. PCT/KR2020/003321, filed on Mar. 10, 2020, which claims priority under 35 U.S.C. 119(a) to Patent Application No. 10-2019-0029845, filed in the Republic of Korea on Mar. 15, 2019 and Patent Application No. 10-2019-0120852 (now patented as KR 10-2292657 B1 issued Aug. 17, 2021), filed in the Republic of Korea on Sep. 30, 2019, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2021-06-02_1183-0140PUS1_ST25.txt" created on Jun. 2, 2021 and is 19,997 bytes in size. The sequence listing contained in this .txt file is part of the specification and is hereby incorporated by reference herein in its entirety.

TECHNICAL FIELD

The present disclosure relates to a genetically modified immunocyte expressing a chimeric antigen receptor (CAR) comprising an antigen binding domain specifically binding to cancer cells or producing TNF-related apoptosis-inducing ligand (TRAIL) protein, a composition for preventing or treating cancer, the composition comprising the immunocyte, a cell therapeutic agent, a method of providing information for cancer diagnosis, and a method of preparing the genetically modified immunocyte.

BACKGROUND ART

Cancer immunotherapy, which has recently emerged, exploits human body's own immune system to more specifically remove cancer cells while minimizing damage to normal cells, and several sub-fields (antibody therapy, immunocyte therapy, viral immunotherapy, nanotechnology immunotherapy, etc.) are actively being studied. Among them, the immunocyte therapy is a method of treating cancer by increasing the number of cells, such as natural killer cells, natural killer T cells, T cells, B cells, dendritic cells, etc., among lymphocytes obtained from a patient's blood, potentiating their functions in vitro, and then returning them to the patient's body. This therapy of using immunocytes has been considered to exhibit good effects on modulation of immune responses and to be excellent in terms of toxicity and safety.

In recent years, there has been a growing interest in, as the immunocyte therapies, cell therapeutic methods in which immunocytes are taken out of a body, potentiated or genetically modified, and then put back into the body. Representative examples thereof comprise tumor infiltrating lymphocyte (TIL), chimeric antigen receptor (CAR), T cell receptor (TCR) techniques, etc., and in particular, studies have been actively conducted on CAR which is an artificial receptor by genetic recombination.

CAR is an artificial receptor designed to deliver antigen specificity to T cells. CAR comprises an antigen-specific component, a transmembrane component, and an intracellular component, which are selected to activate T cells and to provide specific immunity. CAR-expressing T cells may be used in various therapies comprising cancer therapy.

Therapeutic agents such as CAR-T are effective against tumors. However, in some cases, these treatments have caused side effects due to partial non-specific attacks on healthy tissues. In order to overcome this problem, third-generation CAR-T is currently studied, in which two signal domains serving as a co-stimulatory signal and an artificial receptor (additional engineered receptor) are added to increase 'cancer cell antigen-recognizing ability' so that side effects of attacking normal cells are minimized.

Nevertheless, development of CAR-T cell therapeutic agents is hampered due to the following problems: current CAR-T techniques have limitations that CAR-T is produced to recognize only one protein expressed in cancer cells, and thus too much cost is required to develop individual therapeutic agents; once CAR-T is injected, toxic T cells continue to function and cause toxicity even after cancer cells have been removed; and in a case where there are normal cells presenting a target protein, CAR-T induces a non-specific attack thereon to cause a fatal side effect which is not reversible.

Therefore, the immunocyte therapy using NK cells has an advantage in that it is the only cell therapy capable of using other people's immunocytes without side effects, and there is a growing interest therein. For this reason, tumor immunotherapy using patients' immune systems has been steadily developed over the past 10 years, and 'cell therapy products' have been commercialized by using the same. Accordingly, to promote personalized therapies for patients, there is a growing interest in cell therapies in which CAR-introduced immunocytes (e.g., CAR-NK cells) are isolated from blood of a healthy normal person, cultured, and then injected to a cancer patient.

DESCRIPTION OF EMBODIMENTS

Technical Problem

An aspect provides a genetically modified immunocyte expressing a chimeric antigen receptor (CAR) comprising an antigen binding domain specifically binding to cancer cells and/or TNF-related apoptosis-inducing ligand (TRAIL).

An aspect provides a genetically modified immunocyte producing TRAIL protein.

An aspect provides a pharmaceutical composition for preventing or treating cancer, the pharmaceutical composition comprising the genetically modified immunocyte as an active ingredient.

An aspect provides a cell therapeutic agent comprising the genetically modified immunocyte as an active ingredient.

Another aspect provides a method of providing information for cancer diagnosis, the method comprising contacting the genetically modified immunocyte with a sample isolated from an individual.

Still another aspect provides a method of preparing a genetically modified immunocyte, the method comprising introducing a recombinant vector comprising i) an antigen binding domain specifically binding to cancer, ii) a TRAIL gene, or iii) a combination thereof into immunocytes isolated from a human body.

Still another aspect provides a method of preventing or treating cancer, the method comprising administering the genetically modified immunocytes to an individual in need thereof.

Solution to Problem

To achieve the above object, provided is a genetically modified immunocyte expressing a chimeric antigen receptor (CAR) comprising an antigen binding domain specifically binding to cancer cells.

Provided is a genetically modified immunocyte producing TNF-related apoptosis-inducing ligand (TRAIL) protein.

Provided is a pharmaceutical composition for preventing or treating cancer, the pharmaceutical composition comprising the genetically modified immunocyte as an active ingredient.

Provided is a cell therapeutic agent comprising the genetically modified immunocyte as an active ingredient.

Provided is a method of providing information for cancer diagnosis, the method comprising contacting the genetically modified immunocyte with a sample isolated from an individual.

Provided is a method of preparing a genetically modified immunocyte, the method comprising introducing a recombinant vector comprising i) an antigen binding domain specifically binding to FOLR1, ii) a TRAIL gene, or iii) a combination thereof into immunocytes isolated from a human body.

Still another aspect provides a method of preventing or treating cancer, the method comprising administering the genetically modified immunocytes to an individual in need thereof.

ADVANTAGEOUS EFFECTS OF DISCLOSURE

When genetically modified immunocytes according to an aspect are used, excellent cytotoxicity against cancer cells comprising FOLR1, DR4, DR5, or a combination thereof is recognized, and thus the genetically modified immunocytes may be effectively applied as an anticancer agent. Accordingly, the genetically modified immunocytes prepared according to an aspect exhibit anticancer effect with high efficiency, and thus they may be usefully applied to gene therapy.

MODE OF DISCLOSURE

Figure 1:
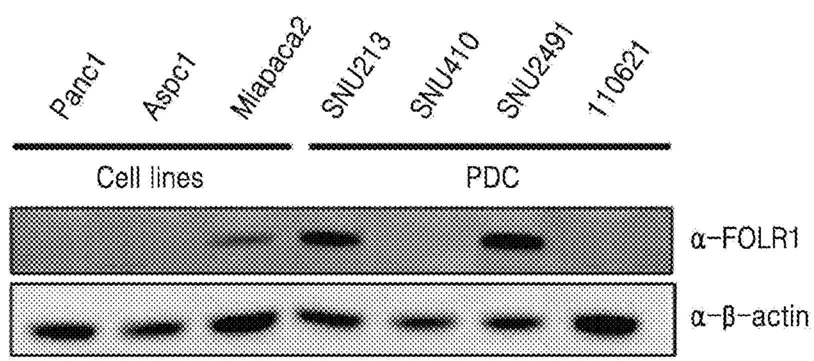
FIG. 1 shows Western blotting experimental results of examining FOLR1 expression in PANC-1, Aspc1, and Miapaca2 which are pancreatic cancer cell lines and SNU 213, SNU 410, SNU 2491, and 110621 which are patient-derived cancer cell lines (PDC)

An aspect provides a genetically modified immunocyte expressing a chimeric antigen receptor (CAR) comprising an antigen binding domain specifically binding to cancer cells and/or TNF-related apoptosis-inducing ligand (TRAIL).

The immunocyte may be any one selected from the group consisting of macrophage, B lymphocyte, T lymphocyte, mast cell, monocyte, dendritic cell, eosinophil, natural killer cell, basophil, and neutrophil.

The "natural killer cell (NK cell)" is a kind of white blood cells in the blood that is responsible for innate immunity, and is also called 'natural killer cell'. The NK cell has a main function of directly attacking and eliminating virus-infected cells or cancer cells. In particular, NK cells are known to effectively control cancer stem cells, which play the most important role in cancer recurrence, in addition to preventing cancer cells from developing, proliferating, and metastasis by attacking cancer cells. In the academic field, chemotherapy using NK cells has been continuously studied, and recently, there is a growing need for research into CAR-NK introduced with chimeric antigen receptors.

Kinds of the cancer cell antigen, i.e., cancer-associated antigen may comprise folate receptor alpha (FOLR1), HER2, HER2/neu, NKG2D, PSMA, CEA, IL13Roc2, EphA2, BCMA, CSPG4, CD138, survivin, CD19, CD20, CD22, k light chain, CD30, CD33, CD123, CD38, ROR1, ErbB2, ErbB3/4, ErbB dimers, EGFr vIII, carcinoembryonic antigen, EGP2, EGP40, mesothelin, TAG72, PSMA, NKG2D ligands, B7-H6, IL-13 receptor a2, MUC 1, MUC 16, CA9, GD2, GD3, HMW-MAA, CD171, Lewis Y, G250/CAIX, HLA-Al MAGE Al, HLA-A2 NY-ESO-1, PSCA, folate receptor-a, CD44v6, CD44v7/8, avb6 integrin, 8H9, NCAM, VEGF receptors, 5T4, Baff, GPC2, CD56, Foetal AchR, NKG2D ligands, or CD44v6.

The chimeric antigen receptor may comprise an antigen binding domain specifically binding to the antigen mentioned above.

In a specific embodiment, the chimeric antigen receptor may be antigen binding domain specifically binding to FOLR1.

The FOLR1 protein is encoded by FOLR1 gene, and known as a member of the folate receptor (FOLR) family. The protein is known to have high affinity for folic acid and several folic acid derivatives and to mediate intracellular delivery of 5-methyltetrahydrofolate.

The genetically modified immunocyte, e.g., natural killer cell, comprises those introduced by a recombinant vector comprising a sequence encoding a chimeric antigen receptor. The term “vector” refers to a means for expressing a target gene in a host cell. For example, the vector comprises a plasmid vector, a cosmid vector, and a virus vector selected from the group consisting of a bacteriophage vector, a herpes simplex virus vector, a vaccinia virus vector, an adenovirus vector, a retrovirus vector, a lentivirus expression vector and an adeno-associated virus vector. A vector which may be used as the recombinant vector may be, for example, prepared by manipulating a plasmid commonly used in the art such as pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc., a phage such as λgt4AB, λ-Charon, λΔz1, phages such as M13., or a virus such as SV40, etc.

In the recombinant vector, a polynucleotide sequence encoding the fusion protein may be operatively linked to a promoter. The term “operatively linked” means a functional linkage between a nucleotide expression control sequence such as a promoter sequence and other nucleotide sequences. Thus, the control sequence may regulate transcription and/or translation of the other nucleotide sequences.

The recombinant vector may be a vector for expression, which may stably express the fusion protein in a host cell. The vector for expression may be a vector commonly used in the art for expressing a foreign protein in a plant, an animal, or a microorganism. The recombinant vector may be constructed using various methods known in the art.

The recombinant vector may be constructed using prokaryotic or eukaryotic cells as a host. For example, when the vector of the present disclosure is a vector for expression and a prokaryotic cell is used as a host cell, the vector generally comprises a strong promoter capable of initiating transcription (e.g., pLλ promoter, trp promoter, lac promoter, tac promoter, T7 promoter, etc.), a ribosome binding site for initiating translation, and a transcription/translation termination sequence. When a eukaryotic cell is used as a host cell, an origin of replication which is comprised in the vector and acts in the eukaryotic cell may comprise f1 origin of replication, SV40 origin of replication, pMB1 origin of replication, adeno origin of replication, AAV origin of replication, BBV origin of replication, etc., but is not limited thereto. Further, a promoter derived from genomes of mammalian cells (e.g., a metallothionein promoter) or a promoter derived from mammalian viruses (e.g., an adenovirus late promoter, a vaccinia virus 7.5K promoter, a SV40 promoter, a cytomegalovirus promoter, and a tk promoter of HSV) may be used, and a transcription termination sequence may be, in general, a polyadenylation sequence.

The cell, for example, eukaryotic cell may be yeasts, fungi, protozoa, cells from plants, higher plants, insects, or amphibians, mammalian cells such as CHO, HeLa, HEK293, and COS-1, and for example, the cell may be cultured cells (in vitro), graft cells, primary cell culture (in vitro and ex vivo), in vivo cells, or mammalian cells comprising human cells, which are commonly used in the art. Further, the organism may be a yeast, a fungus, a protozoa, a plant, a higher plant, an insect, an amphibian, or a mammal.

The genetically modified immunocyte, e.g., genetically modified natural killer cell expressing CAR (hereinafter, referred to as “CAR-NK or CAR-natural killer cell”) is not only capable of solving, through a reaction on/off switch, problems with cancer immunotherapy using existing CAR-T therapeutic agents such as persistent toxicity, risk of autoimmune disease, graft-versus-host disease (GVHD) for xenogeneic cell transplantation, and non-target toxicity, etc., but also is advantageous in that it allows various cancer cells to be targeted, and thus may be utilized as a general-purpose therapeutic agent. Since the CAR-NK cell is capable of allogeneic transplantation, highly efficient cells may be premade, as compared with CAR-T that uses the patient’s own immunocytes. Thus, the CAR-NK cell not only shortens timing of administration of a therapeutic agent to increase therapeutic efficacy thereof, but also may be usefully used for development of therapeutic agents for various diseases due to reduction of development and treatment costs.

As used herein, “antibody” refers to a substance produced by stimulation with an antigen in the immune system, and the type thereof is not particularly limited. Further, in the present specification, the antibody comprises, but is not limited to, Fragments of the antibody which retain an antigen-binding ability, such as Fab, Fab', F(ab')2, and Fv, etc.

“Chimeric antibody” refers to an antibody of which variable regions or complementarity determining regions (CDRs) thereof are derived from an animal that is different from the rest of the antibody.

Such an antibody may be, for example, an antibody of which variable regions are derived from an animal (e.g., a mouse, a rabbit, poultry, etc.) other than a human and of which constant regions are derived from a human. Such a chimeric antibody may be produced by methods, such as genetic recombination, etc., known in the art.

The “heavy chain” refers to both a full-length heavy chain and a Fragment thereof, in which the full-length heavy chain comprises a variable region domain VH having an amino acid sequence of a variable region which is sufficient to confer specificity to an antigen, and three constant region domains, CH1, CH2, and CH3.

As used herein, “light chain” refers to both a full-length light chain and a Fragment thereof, in which the full-length light chain comprises a variable region domain VL having an amino acid sequence of a variable region which is sufficient to confer specificity to an antigen, and a constant region domain CL.

The antigen binding domain comprised in the chimeric antigen receptor according to an aspect refers to a site where a main signal is transduced, the site being located outside the cell membrane and recognizing a cell membrane ligand (a substance that binds to and activates a receptor) of a target cell having a specific antigen. In a specific embodiment, an antigen binding domain specifically binding to FOLR1 was used, in which the antigen binding domain may be an antibody or antibody Fragment specifically binding to FOLR1. Further, the antibody Fragment may be scFv, and the antibody Fragment may be, for example, a nucleotide sequence represented by SEQ ID NO: 1, but is not limited thereto.

The chimeric antigen receptor according to an aspect may comprise an intracellular signaling domain.

As the intracellular signaling domain which is a component of the chimeric antigen receptor, any intracellular signaling domain known in the art may be used without limitation. In a specific embodiment of the present disclosure, the intracellular signaling domain may be a co-stimulatory domain, CD3z, or a combination thereof, but is not limited thereto. The co-stimulatory domain may be one or more selected from the group consisting of ICOS, CD27, CD28, 4-1BB, and OX40.

The chimeric antigen receptor according to an aspect employs the co-stimulatory domain, CD3z, or a combination thereof as the intracellular signaling domain so that NK cell may exhibit a killing effect on cancer cells with high activity. The CD3z(zeta) may function as an NK cell activation domain. Among the co-stimulatory domains, CD27 may be, for example, a nucleotide sequence represented by SEQ ID NO: 2, and CD3z may be, for example, a nucleotide sequence represented by SEQ ID NO: 3, but are not limited thereto. In a specific embodiment, the chimeric antigen receptor may be, for example, a nucleotide sequence represented by SEQ ID NO: 6.

An aspect provides a genetically modified immunocyte producing TRAIL protein.

The recombinant vector according to an aspect further comprises TRAIL gene to allow production of TRAIL protein in cells into which the recombinant vector is introduced. Further, the genetically modified immunocyte, e.g., genetically modified natural killer cell producing TRAIL protein may be obtained by introducing the recombinant vector comprising TRAIL gene. The TRAIL gene may be, for example, a nucleotide sequence represented by SEQ ID NO: 4, but is not limited thereto.

The genetically modified immunocyte according to an aspect may exhibit cytotoxicity against cancer cells expressing i) a cancer cell-specific antigen (e.g., FOLR), ii) DR4 or DR5, or iii) a combination thereof.

In a specific embodiment, the genetically modified immunocyte, e.g., genetically modified natural killer cell by introduction of the recombinant vector comprising a single chain variable Fragment of FOLR1 antibody and TRAIL was found to exhibit excellent anticancer effects against various cancer cells, as compared with those of a recombinant vector comprising a single chain variable Fragment of FOLR1 antibody or TRAIL (Example 3). Further, the NK cell expressing CAR according to an aspect has an excellent cytotoxic effect against cancer cells expressing FOLR.

An aspect provides a pharmaceutical composition for preventing or treating cancer, the pharmaceutical composition comprising the genetically modified immunocyte as an active ingredient.

An aspect provides a pharmaceutical composition comprising the genetically modified immunocyte, e.g., genetically modified natural killer cell, which expresses CAR comprising the antigen binding domain specifically binding to cancer cells or produces TRAIL protein. The pharmaceutical composition may be used for preventing and/or treating cancer.

The term “preventing” means all actions by which a cause of cancer is eliminated or detected at early stage to prevent the corresponding disease.

The term “treating” means all actions by which symptoms of cancer have taken a turn for the better or been modified beneficially.

The term ‘cancer’ refers to a group of diseases having characteristics in which when a normal cell death balance is broken, cells become hyperproliferative and invade surrounding tissues. The cancer may be, for example, one or more selected from the group consisting of carcinoma originating from epithelial cells such as skin cancer, lung cancer, larynx cancer, stomach cancer, large intestine/rectal cancer, liver cancer, gallbladder cancer, pancreatic cancer, breast cancer, ovarian cancer, uterine cancer, cervical cancer, prostate cancer, kidney cancer, sarcoma originating from connective tissue cells, bone cancer, muscle cancer, fat cancer, fibrous cell cancers, blood cancer originating from hematopoietic cells, such as multiple myeloma, leukemia, lymphoma, and tumors originating from nervous tissues, but is not limited thereto.

The pharmaceutical composition comprising the genetically modified immunocyte, e.g., genetically modified natural killer cell expressing CAR comprising the antigen binding domain specifically binding to cancer cells or producing TRAIL protein according to an aspect exhibits an excellent cancer cell-killing effect against cancer cells expressing i) a cancer cell-specific antigen (e.g., FOLR), ii) DR4 or DR5, or iii) a combination thereof.

In addition to the genetically modified immunocyte expressing CAR comprising the antigen binding domain specifically binding to cancer cells or producing TRAIL protein, the pharmaceutical composition for preventing or treating cancer may further comprise a pharmaceutically acceptable carrier, i.e., saline, sterile water, Ringer’s solution, buffered saline, cyclodextrin, a dextrose solution, a maltodextrin solution, glycerol, ethanol, liposome, or a mixture of one or more thereof, and if necessary, other common additive such as an antioxidant, a buffer, etc. Furthermore, the pharmaceutical composition may be formulated into injectable formulations such as aqueous solutions, suspensions, emulsions, etc., pills, capsules, granules, or tablets, by additionally adding a diluent, a dispersant, a surfactant, a binder, and/or a lubricant. Moreover, the pharmaceutical composition may be formulated according to respective components using an appropriate method known in the art or a method disclosed in Remington’s Pharmaceutical Science (Mack Publishing Company, Easton Pa.). The formulations of the pharmaceutical composition of the present disclosure are not particularly limited, but the pharmaceutical composition may be formulated into injections or inhalable forms.

The administration method of the pharmaceutical composition according to an aspect is not particularly limited, but the pharmaceutical composition may be administered parenterally or orally such as intravenously, subcutaneously, intraperitoneally, via inhalation, or topically according to an aimed method. An administration dose may vary depending on a patient’s weight, age, gender, health conditions, diet, administration time, administration route, excretion rate, severity of a disease, etc. A daily dose means an amount of the therapeutic material according to an aspect which is sufficient to treat for palliated conditions of a disease when it is administered to an individual in need thereof. An effective dose of the therapeutic material may vary depending on particular compounds, disease condition and severity, and an individual in need of treatment, and may be generally determined by those skilled in the art. For non-limiting example, a dose of the composition according to an aspect administered to a human body may vary depending on a patient’s age, weight, gender, administration route, health condition, and severity of disease. Based on an adult patient weighing 70 kg, for example, about 1,000 cells/time to about 10,000 cells/time, about 1,000 cells/time to about 100,000 cells/time, about 1,000 cells/time to about 1000,000 cells/time, about 1,000 cells/time to about 10,000,000, about 1,000 cells/time to about 100,000,000 cells/time, about 1,000 cells/time to about 1,000,000,000 cells/time, about 1,000 cells/time to about 10,000,000,000 cells/time, may be administered once a day to several times a day at regular intervals, or may be administered several times at regular intervals.

The ‘individual’ refers to a subject in need of treatment of cancer, vascular diseases, or inflammatory diseases, and more specifically, a mammal such as a human, or non-human mammals such as primates, mice, rats, dogs, cats, horses, cows, etc.

The pharmaceutical composition according to an aspect provides a pharmaceutical composition comprising the genetically modified immunocyte expressing CAR comprising the antigen binding domain specifically binding to cancer cells or producing TRAIL protein. Further, when the immunocytes are comprised as an active ingredient, they may be used as a cell therapeutic agent for treating and preventing cancer. The pharmaceutical composition or the cell therapeutic agent may be used in preventing and/or treating cancer.

An aspect provides a cell therapeutic agent comprising the genetically modified immunocyte as an active ingredient.

The term "cell therapeutic agent" refers to a therapeutic agent which is used for the suppression of cancer by using autologous, allogenic, and xenogenic cells for restoring functions of tissues. When the immunocyte, e.g., the genetically modified natural killer cell is comprised as an active ingredient, it may be used as a cell therapeutic agent for treating and preventing cancer.

The cell therapeutic agent may further comprise a pharmaceutically acceptable carrier. The pharmaceutically acceptable carrier may be, for example, saline, sterile water, Ringer's solution, buffered saline, a dextrose solution, a maltodextrin solution, glycerol, ethanol, human serum albumin (HSA) and a mixture of one or more thereof. If necessary, other common additives such as an antioxidant, a buffer, a bacteriostatic agent, etc. may be added.

Further, to the cell therapeutic agent, if necessary, a suspending agent, a solubilizing aid, a stabilizer, an isotonic agent, a preservative, an adsorption inhibitor, a surfactant, a diluent, an excipient, a pH adjuster, an analgesic agent, a buffer, a sulfur-containing reducing agent, an antioxidant, etc. may be appropriately added, depending on the formulation. Examples of the suspending agent may comprise methyl cellulose, polysorbate 80, hydroxyethyl cellulose, gum arabic, powdered tragacanth, sodium carboxy methyl cellulose, polyoxyethylene sorbitan monolaurate, etc.

Examples of the solubilizing aid may comprise polyoxyethylene hydrogenated castor oil, polysorbate 80, nicotine acid amide, polyoxyethylene sorbitan monolaurate, macrogol, ethyl ester of castor oil fatty acid, etc. Examples of the stabilizer may comprise dextran 40, methyl cellulose, gelatin, sodium sulfite, sodium metasulfite, etc.

The isotonic agent may comprise, for example, D-mannitol, sorbitol, etc.

The preservative may comprise, for example, methyl paraoxybenzoate, ethyl paraoxybenzoate, sorbic acid, phenol, cresol, chlorocresol, etc.

The adsorption inhibitor may comprise, for example, human serum albumin, lecithin, dextran, ethylene oxide/propylene oxide copolymers, hydroxypropyl cellulose, methyl cellulose, polyoxyethylene hydrogenated castor oil, polyethylene glycol, etc.

The sulfur-containing reducing agent may comprise, for example, N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and thioalkanoic acid having 1 to 7 carbon atoms those having a sulfhydryl group.

The antioxidant may comprise, for example, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as ethylenediaminetetraacetic acid (EDTA), sodium pyrophosphate, sodium metaphosphate, etc.

Based on an adult patient weighing 70 kg, the cell therapeutic agent may be administered, for example, at a dose of about 1,000 cells/time to about 10,000 cells/time, about 1,000 cells/time to about 100,000 cells/time, about 1,000 cells/time to about 1000,000 cells/time, about 1,000 cells/time to about 10,000,000, about 1,000 cells/time to about 100,000,000 cells/time, about 1,000 cells/time to about 1,000,000,000 cells/time, about 1,000 cells/time to about 10,000,000,000 cells/time, once a day to several times a day at regular intervals, or may be administered several times at regular intervals.

The injection product according to the present disclosure may be prepared in a filled injection form by taking a quantity commonly known in the art, the quantity varying depending on constitution and kinds of defects of patients.

The term "therapeutic agent" or "pharmaceutical composition" refers to a molecule or compound that confers some beneficial effects upon administration to a subject. The beneficial effects comprise enablement of diagnostic determinations; amelioration of a disease, symptom, disorder, or pathological condition; reducing or preventing the onset of a disease, symptom, disorder, or illness; and counteracting a disease, symptom, disorder, or pathological condition.

As used herein, the term "treatment" or "treating", or "palliating" or "ameliorating" may be used interchangeably. These terms refer to methods of obtaining beneficial or wanted results comprising, but not limited to, a therapeutic benefit and/or a prophylactic benefit. The therapeutic benefit indicates any therapeutically relevant improvement in or effect on one or more diseases, illnesses, or symptoms under treatment. For prophylactic benefit, the compositions may be administered to a subject at risk of developing a particular disease, illness, or symptom, or to a subject reporting one or more of the physiological symptoms of a disease, even though the disease, illness, or symptom may not have yet been manifested.

The term "effective amount" or "therapeutically effective amount" refers to an amount of an agent that is sufficient to cause beneficial or wanted results. The therapeutically effective amount may vary according to one or more of a subject and a disease condition being treated, the subject's weight and age, severity of the disease condition, and administration mode, which may be easily determined by one of ordinary skill in the art. Also, the term may be applied to a dose that will provide an image for detection by any one of the imaging methods described herein. A particular dose may vary according to one or more of a particular agent chosen, a dosing regimen to be followed, whether it is administered in combination with other compounds, timing of administration, a tissue to be imaged, and a physical delivery system in which it is carried.

In a specific embodiment, when the genetically modified immunocyte expressing CAR-NK is administered in combination with TRAIL, it exhibits a synergistic effect.

Still another aspect provides a method of providing information for cancer diagnosis, the method comprising contacting the genetically modified immunocyte with a sample isolated from an individual.

Still another aspect provides a composition for diagnosing cancer and a kit for diagnosing cancer, each comprising the genetically modified immunocyte, e.g., genetically modified natural killer cell expressing CAR comprising the antigen binding domain specifically binding to folate receptor alpha (FOLR1) or producing TRAIL protein according to an aspect. Still another aspect provides a method of providing information for cancer diagnosis, the method comprising contacting, with a sample isolated from an individual, the composition comprising the genetically modified immunocyte expressing CAR comprising the antigen binding domain specifically binding to FOLR1 or producing TRAIL protein according to an aspect.

The term "diagnosis" comprises determining susceptibility of an individual to a particular disease or illness, determining whether an individual currently has a particular disease or illness, determining prognosis of an individual suffering from a particular disease or illness, or therametrics (e.g., monitoring status of an individual to provide information about therapeutic efficacy).

Still another aspect provides a method of preparing the genetically modified immunocyte, e.g., genetically modified natural killer cell, the method comprising introducing a recombinant vector comprising i) an antigen binding domain specifically binding to cancer cells, ii) a TRAIL gene, or iii) a combination thereof into immunocytes isolated from a human body.

Still another aspect provides a method of preventing or treating cancer, the method comprising administering the genetically modified immunocytes to an individual in need thereof.

The method may further comprise administering TRAIL in combination, and the TRAIL may be administered concurrently, separately, or sequentially with the immunocyte. When the genetically modified immunocyte and TRAIL are administered in combination of two active ingredients, the therapeutic effect on cancer may be additive or synergistic. The genetically modified immunocyte may be administered to an individual in need thereof via various routes. All modes of administration may be contemplated, for example, administration may be made orally, rectally or by intravenous, intramuscular, subcutaneous, endometrial, or intracerebroventricular injection.

The redundant contents are omitted in consideration of complexity of the present specification, and the terms not otherwise defined in the present specification have the meanings commonly used in the technical field to which the present disclosure pertains.

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1. Identification of Cancer Cell-Specific Target Antigen

To select target antigens commonly expressed in various kinds of cancer cells, experiments to identify markers expressed in PANC-1, Aspc1, and Miapaca2 which are pancreatic cancer cell lines and SNU213, SNU 410, SNU 2491, and 110621 which are patient-derived cell lines (PDC) were performed by Western blotting and fluorescence activated cell sorter (FACS) analysis.

After pretreatment for analysis of PANC-1, Aspc1, and Miapaca2 which are pancreatic cancer cell lines and SNU213, SNU 410, SNU 2491, and 110621 which are PDC, they were lysed by adding an RIPA lysis buffer (Sigma) supplemented with a protease inhibitor (Thermo Scientific). A total of 50 μg of proteins was analyzed for immunoblotting, and incubated at 4° C. overnight, and detected using an FOLR1-specific primary antibody (ABcam), followed by incubation at room temperature for 2 hr with a horseradish peroxidase-conjugated secondary antibody. The proteins were visualized by chemical illuminance using a Western ECL substrate (Bio-Rad), and the obtained illuminance images were analyzed by LAS-3000 (Fujifilm). Intensity of bands was quantified using an ImageJ software, and results were examined. The results are shown in FIG. 1.

Thereafter, the stained cells were collected using a GUAVA® EASYCYTE™ flow cytometer (Merck Millipore), and analyzed with FLOWJO™ version 10.2 (TreeStar). FOLR1, DR4, and DR5 were detected using APC-conjugated anti-human FOLR1, APC-conjugated anti-human DR4, and PE-conjugated anti-human DR5 antibodies, respectively and subjected to FACS analysis. Results are shown in FIG. 2.

As shown in FIG. 1, FOLR1 was rarely detected in PANC-1 and Aspc1 which are pancreatic cancer cell lines and SNU410 and 110621 which are PDCs. In addition, it was confirmed that α-FOLR1 was weakly detected in Miapaca2, but α-FOLR1 was strongly detected in SNU2491 and SNU213 which are PDCs.

Figure 2:
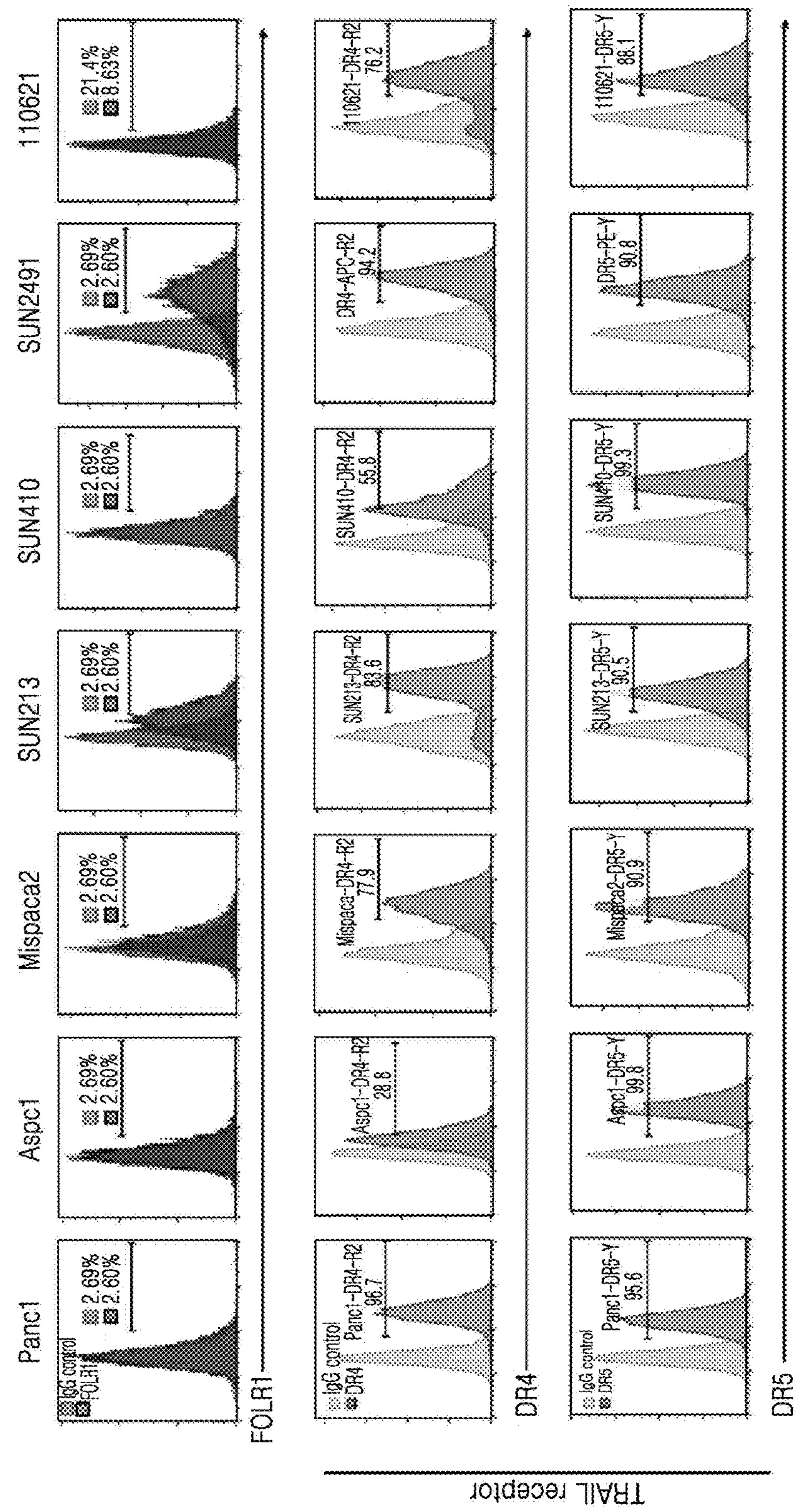
FIG. 2 shows FACS analysis of examining FOLR1, DR4, and DR5 expression in PANC-1, Aspc1, Miapaca2, SNU 213, SNU 410, SNU 2491, and 110621 which are cancer cell lines.

Further, as shown in FIG. 2, examination was also performed with respect to PANC-1, Aspc1, Miapaca2, SNU213, SNU 410, SNU 2491, and 110621 which are cancer cell lines, and as a result, high expression of DR4 and DR5 which are TRAIL receptors was found in all the seven cancer cell lines, unlike FOLR1 expression in some of the cancer cell lines.

Taken together, FOLR1 expression was found only in some of pancreatic cell lines, but TRAIL receptors DR4 and DR5 were found in various kinds of cancer cell lines. Accordingly, it was confirmed that FOLR1 may be used for specifically targeting pancreatic cancer cell lines, and DR4 and DR5 may be used as a cancer cell-specific target antigen marker for targeting more various kinds of cancer cells.

Example 2. Production of Chimeric Antigen Receptor (CAR)-NK Cell

Experiments were designed to examine whether CAR-NK cells expressing FOLR1-specific chimeric antigen receptor confirmed in Example 1 exhibit cancer cell-specific killing effect. DR4 and DR5 identified as markers for various cancer cells are known as TRAIL receptor, and therefore, experiments for CAR-NK production were designed to examine whether various cancer cells may be effectively killed by expressing TRAIL in NK cells capable of exhibiting an anticancer effect by exhibiting cytotoxicity against cancer cells or by preparing CAR-NK expressing FOLR1-specific chimeric antigen receptor together with NK cells expressing TRAIL.

Figure 3:
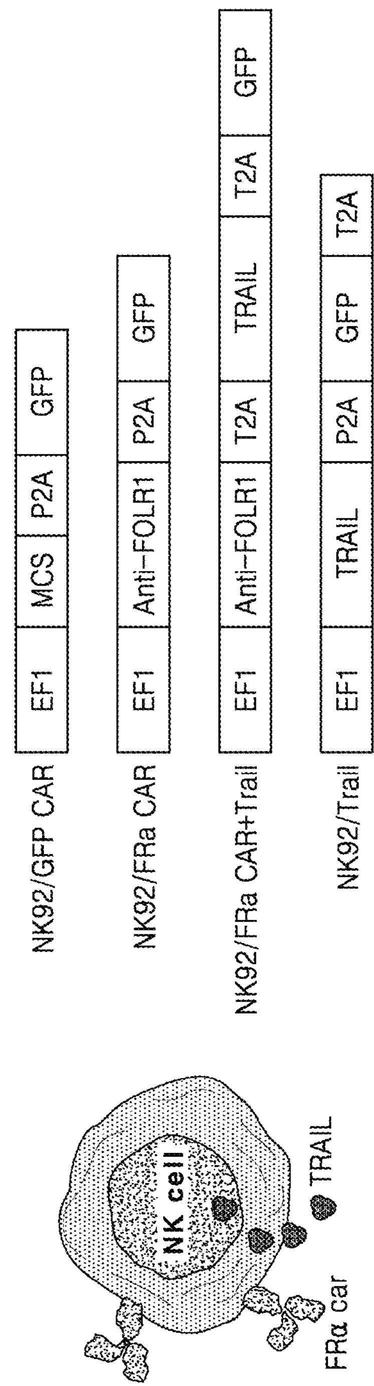
FIG. 3 illustrates transformed NK cells and a vector introduced into NK cells.

A second-generation CAR vector was constructed, the second-generation CAR vector expressing a fusion protein consisting of a single chain variable Fragment (scFv) of FOLR1 antibody and a signaling domain consisting of CD27 and CD3z. FOLR1-CAR DNA comprising scFv of FOLR1, CD27 and CD3z was purchased from Creative biolabs (USA). A lentiviral expression vector comprising pLVXPuro (Cat. #632164) was purchased from Addgene. To produce GFP-expressing CAR-NK direct folate receptor, a CAR vector sequence was prepared by inserting a DNA Fragment containing GFP after the P2A sequence. Thereafter, TRAIL gene was further introduced into the vector, in which scFv against FOLR1 had been introduced, to prepare a vector. In addition, a vector expressing only TRAIL gene was prepared. Each vector was then introduced into GFP-expressing CAR-NK or NK cells, respectively. The transformed NK cells and the vectors introduced into NK cells are shown in FIG. 3, respectively.

Detailed experimental methods are as follows: 293T cells were transfected using a lentiviral expression vector and a viral power lentiviral packaging MIX (Invitrogen, 44-2050) by Invitrogen Lipofectamine 3000 reagent (Invitrogen, L3000-015)-mediated transfection method. 48 hr later, the culture medium was harvested and centrifuged at 1300 rpm for 5 min. The supernatant resulting from centrifugation was passed through a 0.45 μm filter, and added to a solution to which 200 IU/ml of IL-2 and 8 μg/ml of polybrene (santa cruz, sc-134220) were added at a volume ratio of 1:1, and $2\times10^5$ NK-92 cells were incubated with the lentiviral expression vector. 2 μg/ml of puromycin (Sigma-Aldrich, USA) was added to the cells, and incubated for 2 weeks, and then selected. Thereafter, CAR expression was examined in CAR-NK cells prepared through the above selection by fluorescence activated cell sorter (FACS) analysis, western blotting using a primary antibody against α-CD3zeta, and multifocal fluorescence microscopy, and detailed experimental methods are as follows.

Expression in CAR-transfected NK cell line was assessed using a GUAVA® EASYCYTE™ Flow cytometer (Merck Millipore), and analyzed using FLOWJO™ version 10.2 (TreeStar). $2\times10^5$ cells were analyzed and GFP expressing cells were counted using FL1 channel. Further, $3\times10^4$ CAR-transfected NK cells were seeded in an IVID dish, and expression was examined by multifocal fluorescence microscopy (Carl-zeiss, Germany). $3\times10^4$ CAR-transfected NK cells were lysed using a RIPA lysis buffer (Sigma) supplemented with a protease inhibitor (Thermo Scientific). A total of 40 μg of proteins were analyzed for immunoblotting, incubated at 4° C. overnight, and detected using CD3ZETA (Santa cruz, 1:1000), followed by incubation at room temperature for 2 hr with a horseradish peroxidase-conjugated secondary antibody (Bethy Laboratories, 1:5000). Then, the reacted proteins were visualized by chemical illuminance using a Western ECL substrate (Bio-Rad), and the visualized illuminance images were analyzed by LAS-3000 (Fujifilm). Measured intensity of bands was quantified using an ImageJ software, and results thereof are shown in FIGS. 4A, 4B, and 4C.

Figure 4A:
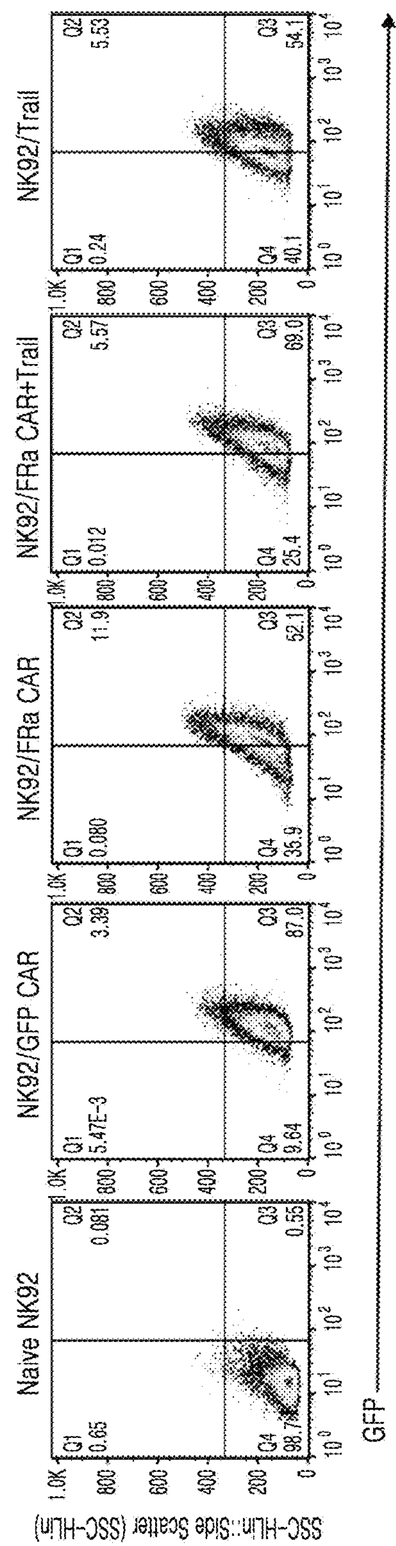
FIG. 4A shows results of FACS analysis of prepared CAR-NK cells.
Figure 4B:
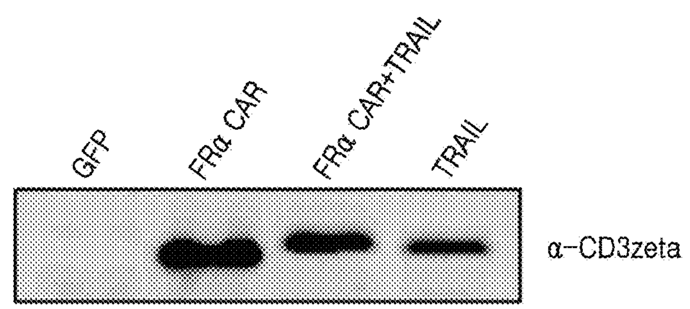
FIG. 4B shows results of Western blotting (FIG. 4B) examined by using a primary antibody against α-CD3zeta.
Figure 4C:
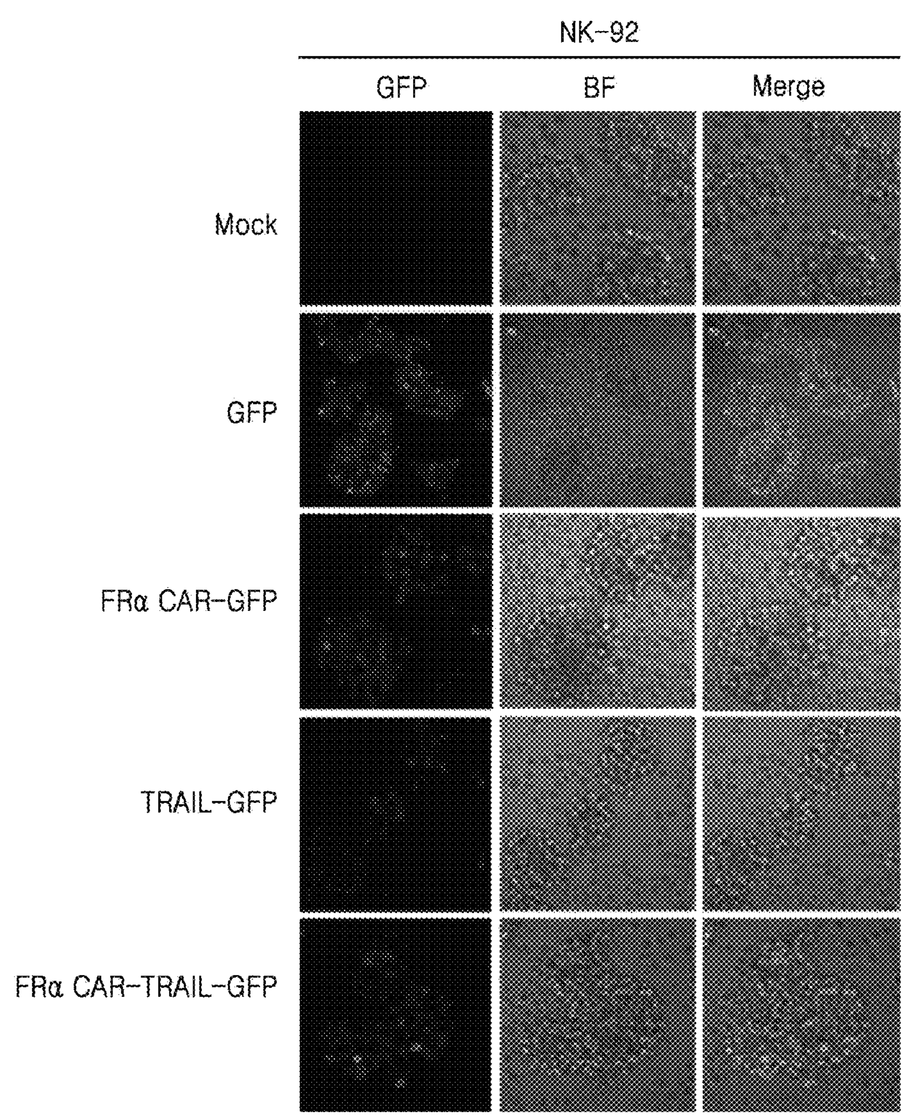
FIG. 4C shows results of examining CAR expression by multifocal fluorescence microscopy.

FIG. 4A shows that CAR-introduced NK cells expressed the CAR of the present disclosure, and TRAIL-introduced NK cells also secreted the material, as confirmed in FIGS. 4B and 4C, indicating that the vector prepared in the present exemplary embodiment is effectively able to genetically modify CAR-NK cells.

Example 3. Examination of Cytotoxicity of Prepared CAR-NK Cell Against Cancer Cell Lines To examine whether the CAR-NK cells prepared in Example 2 actually exhibit anticancer effects on various cancer cells, cytotoxicity assays were performed. CAR-transfected NK-92 cells were added to target cancer cell lines SNU2491 and SNU2469 ($2\times10^5$ cells) which are PDC, at a ratio of 2.5:1 and 5:1, and co-cultured in a culture medium for 4 hr. SNU2491 cell is a cancer cell line with a high level of FOLR1 expression. Thereafter, to visualize the NK cells, they were labeled with FITC-conjugated CD56 (Biolegend). To assess cancer cell-killing effects, the target cells were separated, and stained with aminoactinomycin D (7-AAD) which is a red fluorescent probe labeling dead cells and necrotic target cells in a cytotoxicity assay, followed by analysis using FACS. FITC-CD56-labeled cells were detected in FL1 channel and 7-AAD-stained cells were detected in FL3 channel, and results are shown in FIG. 5A.

Figure 5A:
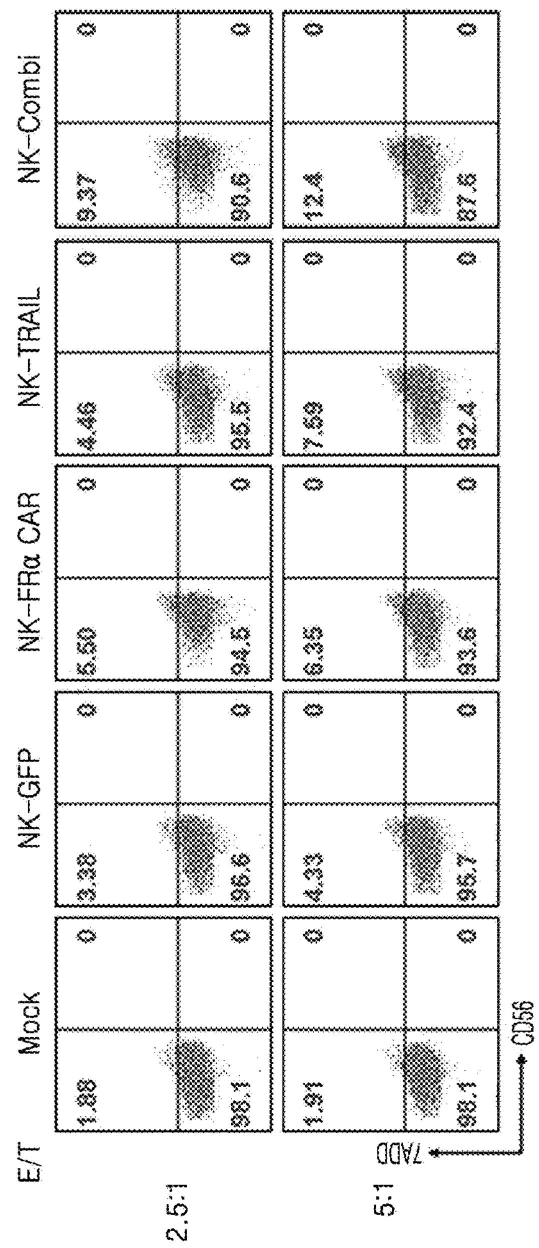
FIG. 5A shows cell-killing effect by treatment of a cancer cell line SNU2491 with the prepared CAR-NK cells.
Figure 5B:
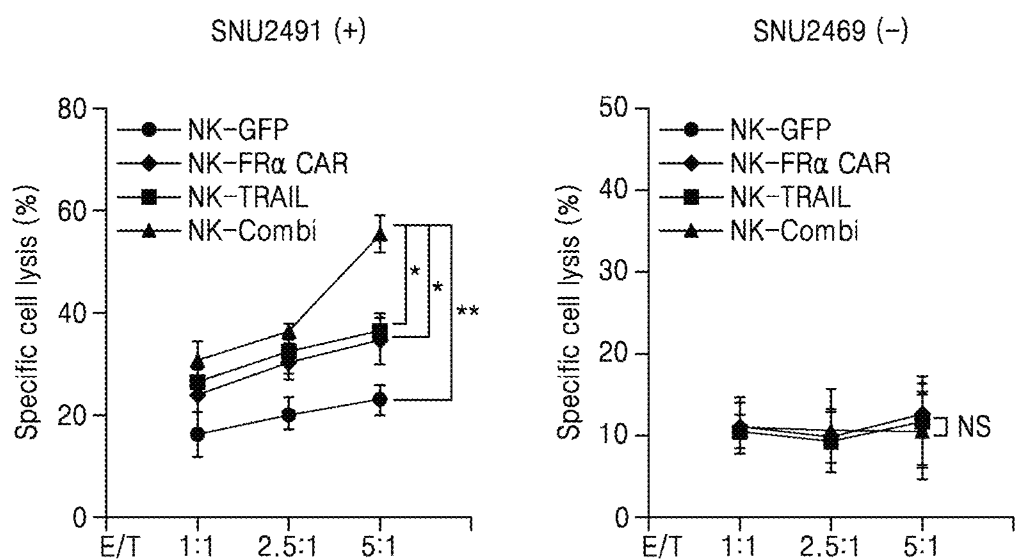
FIG. 5B is a graph showing cell specific killing effects by treatment of SNU2491 and SNU2469 with the prepared CAR-NK cells.

Further, specific cell lysis was examined with respect to a cancer cell line (SNU2469) with low expression of FOLR1 and DR4/5 and a cancer cell line (SNU2491) with high expression of FOLR1 and DR4/5, and shown in FIG. 5B.

As shown in FIG. 5A, it was confirmed that higher cytotoxicity was induced in the cancer cell line SNU2491 with high expression of FOLR1 and DR4/5, when co-cultured with NK cells expressing Fra GFP CAR and TRAIL, as compared with a control group expressing only GFP. Further, a group (NK-Fra CAR) containing scFv of FOLR1 antibody and a group (NK-TRAIL) expressing TRAIL were confirmed to exhibit more excellent cytotoxic effects. In particular, NK cells (NK-Combi) expressing a combination of Fra and TRAIL exhibited an improved synergistic effect, and notably, exhibited an excellent cell-killing effect about twice or higher than that of Fra GFP group.

Further, as shown in FIG. 5B, in SNU2469 with low expression of FOLR1 and DR4/5, there was little difference between the control group (GFP) and the Fra GFP CAR-expressing group. In contrast, in the cancer cell line SNU2491 with high expression of FOLR1 and DR4/5, NK cells (NK-Combi) expressing a combination of Fra and TRAIL exhibited an increased cell-killing effect about twice that of cells expressing Fra or TRAIL.

Taken together, it was confirmed that CAR-NK cells, in this order of CAR-NK cells introduced with Fra GFP vector, CAR-NK cells introduced with TRAIL-GFP vector, and NK cells expressing a combination of Fra and TRAIL (Fra-TRAIL-GFP), exhibited higher cytotoxic effects against cancer cells. With regard to the cancer cell lines to be treated, CAR-NK cells prepared in this exemplary embodiment were confirmed to exhibit more excellent cell-killing effect against the cancer cell lines with high expression of FOLR1 and DR4 and 5.

Example 4. Examination of Cancer Cell Line Proliferation-Inhibitory Effect of Prepared CAR-NK Cells in Animal Cells 4.1 Examination of Cancer Cell Size Reduction Effect in Animal Cells To examine whether CAR-NK cells transfected with CAR prepared in Example 2 are able to effectively inhibit cancer cell proliferation, experiments were performed to measure cancer cell volumes in cancer mouse models into which the CAR-NK cells were injected.

Figure 6A:
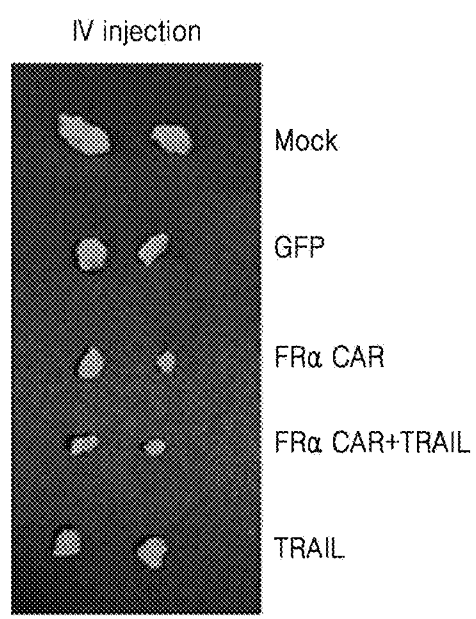
FIG. 6A shows results of examining proliferation-inhibitory effect through cancer cell volume reduction which was observed at 18 days after administering the prepared CAR-NK cells to cancer mouse models.
Figure 6B:
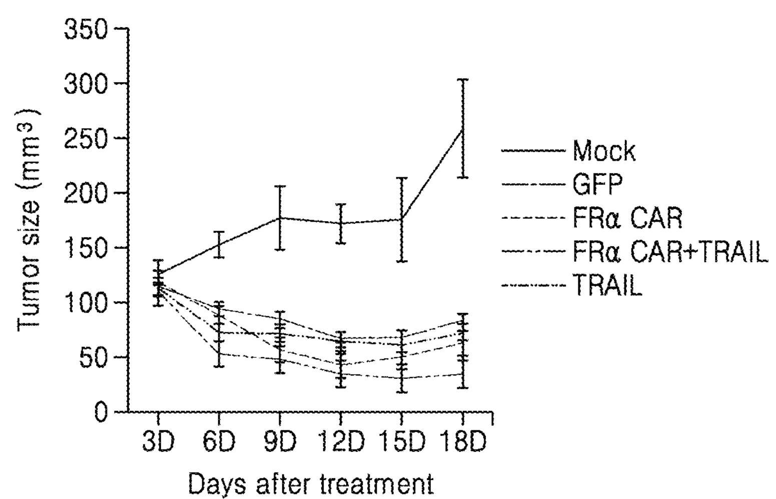
FIG. 6B shows results of measuring tumor volumes at 3 days, 6 days, 9 days, 12 days, 15 days, and 18 days after administering CAR-NK cells.

To prepare cancer mouse models, $1.5\times10^7$ SNU2491 cancer cells were cultured in a medium mixed with a 50% Matrigel solution (BD Biosciences), and then subcutaneously injected into the left flank of female NSG (NOD/SCID/IL-2Rgcnull) mouse. Thereafter, when the tumor size of the mouse reached 0.1 $cm^3$, the cultured NK cells prepared in Example 2 were intravenously administered at a density of $5\times10^6$ cells three times at 3-day intervals. Each individual tumor volume was measured every three days, and the tumor volume was monitored for a total of 18 days, and determined by Equation of $V=(A\times B^2)/2$. In Equation, A represents the largest diameter of the tumor and B represents the shortest diameter of the tumor. At 28 days after administration, the mice were sacrificed and anatomized for further analysis of tumors. Results of measuring the cancer cell volume of the CAR-NK cell-administered group are shown in FIG. 6A, and results of measuring the tumor volume at 3 days, 6 days, 9 days, 12 days, 15 days, and 18 days after administration of CAR-NK cells are shown in FIG. 6B. Mock is a negative control group which was not treated with NK cells.

As shown in FIG. 6A, the group administered with NK cells introduced with GFP and TRAIL showed a reduced volume of cancer cells, as compared with the control Mock. It was confirmed that the Fra GFP CAR-administered group and the Fra GFP+TRAIL-expressing group showed a remarkably reduced volume of cancer cells, as compared with the control Mock. As shown in FIG. 6B, when GFP, TRAIL, and Fra GFP CAR-introduced NK cells were administered, the cancer cell volume showed about 20% reduction at 18 days after administration of the NK cells, as compared with the initial volume. In particular, the Frα GFP+TRAIL-introduced group showed a remarkable reduction in the cancer cell volume from the beginning of transfection, and showed about 60% reduction at 18 days after administration, as compared with the initial volume.

4.2 Examination of Cancer Cell-Killing Effect in Animal Cells

To examine whether the CAR-NK cells transfected with CAR prepared in Example 2 effectively inhibit cancer cell proliferation, TUNEL staining and hematoxylin-eosin (H&E) staining were performed to examine cell death or necrosis of cancer cells in animal models administered with the CAR-NK cells.

Figure 6C:
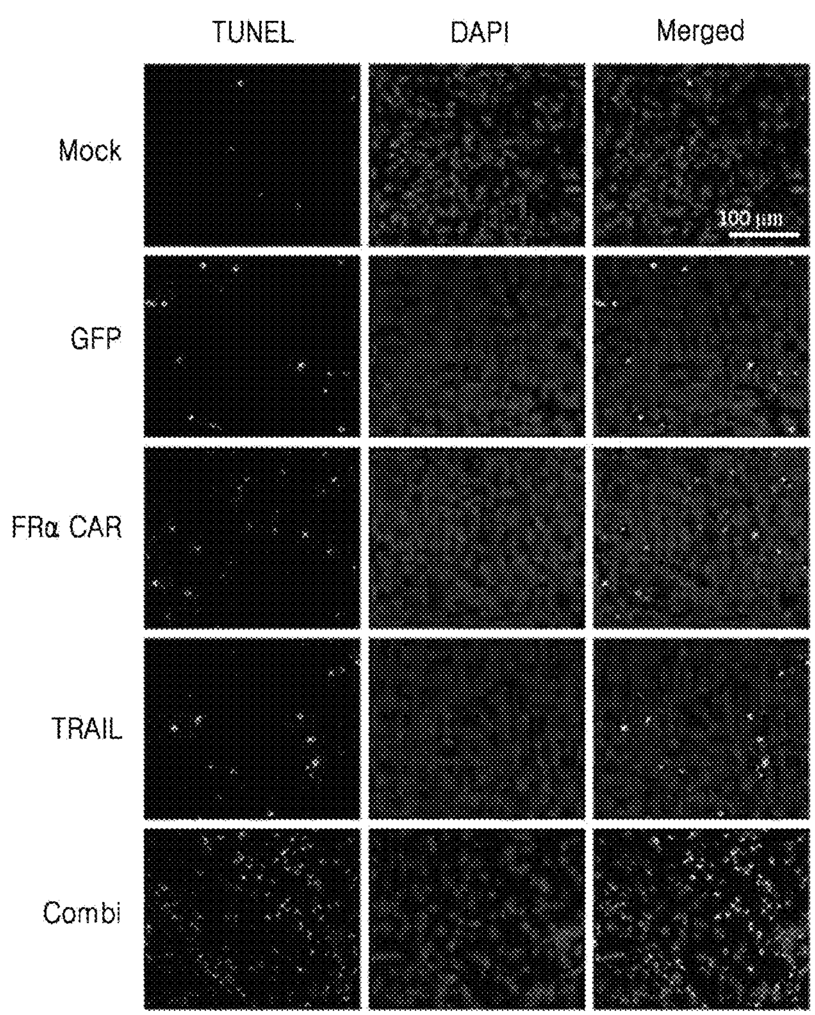
FIG. 6C shows Tunel staining results of examining cell death in groups each treated with GFP, Fra CAR, or TRAIL, and a group treated with a combination of Fra CAR and TRAIL in mice with SNU2491 cancer cells.

To assess cell death of a cancer tissue in vivo, when the mouse tumor size in the animal models prepared in Example 4.1 reached 0.1 $cm^3$, the cultured NK cells prepared in Example 2 were intravenously administered at a density of $5\times10^6$ cells three times at 3-day intervals. 28 days after NK cell administration, the mice were sacrificed and anatomized for further analysis of tumors. TUNEL staining was performed using an in situ cell death detection kit (Roche) according to the manufacturer's instructions. Tumor tissue sections were fixed with 4% paraformaldehyde and permeabilized with 0.1% Triton X-100 and 0.1% sodium citrate. The tumor sections were then incubated in the dark at 37° C. for 1 hr with TUNEL reaction mixture in a humid atmosphere. After washing three times with PBS, slides were mounted with DAPI mounting medium (Vector Laboratories) and examined with a Zeiss LSM 700 confocal microscope, and results examined above are shown in FIG. 6C. Mock is a negative control group which was not treated with NK cells.

Figure 6D:
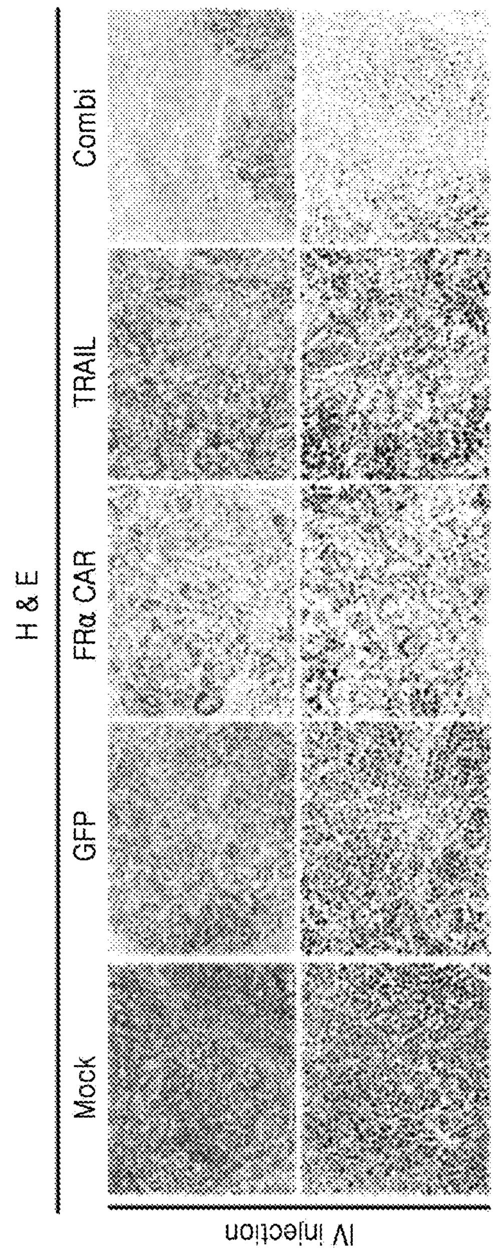
FIG. 6D shows H&E staining results of examining cell death in groups each treated with GFP, Fra CAR, or TRAIL, and a group treated with a combination of Fra CAR and TRAIL.

Twenty-eight days after NK cell administration, H&E staining was also performed. Tumors were fixed overnight in 4% paraformaldehyde, embedded in paraffin, and sliced using a microtome (Leica) so that the tumor sections had a cross section of 6 μm. The prepared sections were deparaffinized with xylene and re-hydrated through graded ethanol washes. Tumor sections were stained with hematoxylin and eosin (H&E) and observed under an optical microscope (Olympus), and results are shown in FIG. 6D. Mock is a negative control group which was not treated with NK cells.

As shown in FIG. 6C, Tunel staining confirmed that cell death was observed in the single treatment group of GFP, Frα CAR, or TRAIL in mice with SNU2491 cancer cells, but cell death of cancer cells was significantly detected in the combination treatment group (Combi) administered with Frα GFP+TRAIL. As shown in FIGS. 6D, H&E staining also confirmed that cancer cell necrosis was significantly increased in the combination treatment group (Combi) administered with Frα and TRAIL in combination, as compared with the single treatment group of GFP, Frα CAR, or TRAIL.

Accordingly, through disease mouse models, it was confirmed that when CAR and TRAIL gene of the present disclosure are introduced and expressed at the same time, increased inhibitory effect on cancer cell proliferation occurred to exhibit remarkable anticancer effect, as compared with that observed in the NK cell group introduced with Frα GFP CAR.

The invention claimed is:

1. A genetically modified immunocyte expressing a chimeric antigen receptor (CAR) comprising an antigen-binding domain specifically binding to cancer cells and TNF-related apoptosis-inducing ligand (TRAIL).

2. The genetically modified immunocyte of claim 1, wherein the genetically modified immunocyte is prepared by introducing a CAR recombinant vector comprising an antigen-binding domain specifically binding to cancer cells.

3. The genetically modified immunocyte of claim 2, wherein the recombinant vector is selected from the group consisting of a plasmid vector, a cosmid vector, a bacteriophage vector, a herpes simplex virus vector, a vaccinia virus vector, an adenovirus vector, a retrovirus vector, a lentivirus expression vector, and an adeno-associated virus vector.

4. The genetically modified immunocyte of claim 1, wherein the CAR comprises an antigen-binding domain specifically binding to folate receptor alpha (FOLR1).

5. The genetically modified immunocyte of claim 1, wherein the antigen-binding domain is an antibody specifically binding to a cancer antigen or a fragment thereof.

6. The genetically modified immunocyte of claim 5, wherein the fragment of the antibody is scFv.

7. The genetically modified immunocyte of claim 1, wherein the genetically modified immunocyte exhibits cytotoxicity against cancer cells expressing a cancer cell-specific antigen.

8. A cell therapeutic agent comprising the genetically modified immunocyte of claim 1 as an active ingredient.

9. A pharmaceutical composition for treating cancer, comprising the genetically modified immunocyte of claim 1 as an active ingredient.

10. The pharmaceutical composition of claim 9, wherein the cancer is one or more selected from the group consisting of carcinoma originating from epithelial cells, lung cancer, larynx cancer, stomach cancer, large intestine/rectal cancer, liver cancer, gallbladder cancer, pancreatic cancer, breast cancer, ovarian cancer, uterine cancer, cervical cancer, prostate cancer, kidney cancer, sarcoma originating from connective tissue cells, bone cancer, muscle cancer, fat cancer, blood cancer originating from hematopoietic cells, leukemia, lymphoma, multiple myeloma, and tumors originating from nervous tissues.

11. A method of providing information for cancer diagnosis, comprising: contacting the genetically modified immunocyte of claim 1 with a sample isolated from an individual wherein the individual is determined to have cancer upon s aid binding between the genetically modified immunocyte and cancer cells and TRAIL.

12. A method of treating cancer, comprising administering the genetically modified immunocyte of claim 1 to an individual in need thereof.

* * * * *

SEQUENCE LISTING

```
<160> NUMBER OF SEQ ID NOS: 6

<210> SEQ ID NO 1
<211> LENGTH: 792
<212> TYPE: DNA
<213> ORGANISM: Artificial Sequence
<220> FEATURE:
<223> OTHER INFORMATION: scFv domain against FOLR

<400> SEQUENCE: 1

atggccctcc ctgtcaccgc cctgctgctt ccgctggctc ttctgctcca cgccgctcgg      60

ccccagctgg ttgaatctgg cggaggactg gtgcagcctg gcagatctct gagactgagc     120

tgtaccacca gcggcttcac cttcggcgac tacgccatga tttgggccag acaggcccct     180

ggcaaaggcc tggaatgggt gtccagcatc agcagcagct ccagctacat ctactacgcc     240

gacagcgtga agggcagatt caccatcagc cgggacaacg ccaagaacag cctgtacctg     300

cagatgaact ccctgagagc cgaggacacc gccgtgtact attgcgccag agagagatac     360

gacttttgga gcggcatgga cgtgtggggc aagggcacaa cagtgacagt ctcttctggc     420

ggcggaggaa gcggaggcgg aggttctggt ggatctgctt ggagtgctct gacacagcct     480

gcctccgtgt ctggatctcc tggccagagc atcacaatca gctgtaccgg caccagctcc     540

gacgtgggca gctacaatct ggtgtcctgg tatcagcaac accccggcaa ggcccctaag     600

ctgatgatct acgagggcag caaaagaccc agcggcgtgt ccaatagatt cagcggcagc     660
```

aagtctggca acgccgcctc tctgacaatc agcggactgc aggctgagga cgaggccgat 720
tactactgcc agagctacga cagcagcctg agcgtggtgt ttggcggagg caccaaactg 780
acagtgctgg ga 792

<210> SEQ ID NO 2
<211> LENGTH: 207
<212> TYPE: DNA
<213> ORGANISM: Artificial Sequence
<220> FEATURE:
<223> OTHER INFORMATION: CD27

<400> SEQUENCE: 2
atccttgtga tcttctctgg aatgttcctt gttttcaccc tggccggggc cctgttcctc 60
catcaacgaa ggaaatatag atcaaacaaa ggagaaagtc ctgtggagcc tgcagagcct 120
tgtcattaca gctgccccag ggaggaggag ggcagcacca tccccatcca ggaggattac 180
cgaaaaccgg agcctgcctg ctccccc 207

<210> SEQ ID NO 3
<211> LENGTH: 337
<212> TYPE: DNA
<213> ORGANISM: Artificial Sequence
<220> FEATURE:
<223> OTHER INFORMATION: CD3 zeta

<400> SEQUENCE: 3
cgcgtgaaat tcagccgcag cgcagatgct ccagcctaca agcaggggca gaaccagctc 60
tacaacgaac tcaatcttgg tcggagagag gagtacgacg tgctggacaa gcggagagga 120
cgggacccag aaatgggcgg gaagccgcgc agaaagaatc cccaagaggg cctgtacaac 180
gagctccaaa aggataagat ggcagaagcc tatagcgaga ttggtatgaa aggggaacgc 240
agaagaggca aaggccacga cggactgtac cagggactca gcaccgccac caaggacacc 300
tatgacgctc ttcacatgca ggccctgccg cctcggg 337

<210> SEQ ID NO 4
<211> LENGTH: 843
<212> TYPE: DNA
<213> ORGANISM: Artificial Sequence
<220> FEATURE:
<223> OTHER INFORMATION: TRAIL gene sequence

<400> SEQUENCE: 4
atggctatga tggaggtcca ggggggaccc agcctgggac agacctgcgt gctgatcgtg 60
atcttcacag tgctcctgca gtctctctgt gtggctgtaa cttacgtgta ctttaccaac 120
gagctgaagc agatgcagga caagtactcc aaaagtggca ttgcttgttt cttaaaagaa 180
gatgacagtt attgggaccc caatgacgaa gagagtatga acagcccctg ctggcaagtc 240
aagtggcaac tccgtcagct cgttagaaag atgattttga gaacctctga ggaaaccatt 300
tctacagttc aagaaaagca acaaaatatt tctcccctag tgagagaaag aggtcctcag 360
agagtagcag ctcacataac tgggaccaga ggaagaagca acacattgtc ttctccaaac 420
tccaagaatg aaaaggctct gggccgcaaa ataaactcct gggaatcatc aaggagtggg 480
cattcattcc tgagcaactt gcacttgagg aatggtgaac tggtcatcca tgaaaaaggg 540
ttttactaca tctattccca aacatacttt cgatttcagg aggaaataaa agaaaacaca 600
aagaacgaca aacaaatggt ccaatatatt tacaaataca caagttatcc tgaccctata 660
ttgttgatga aaagtgctag aaatagttgt tggtctaaag atgcagaata tggactctat 720
tccatctatc aagggggaat atttgagctt aaggaaaatg acagaatttt tgtttctgta 780
acaaatgagc acttgataga catggaccat gaagccagtt ttttcggggc ctttttagtt 840
ggc 843

<210> SEQ ID NO 5
<211> LENGTH: 687
<212> TYPE: DNA
<213> ORGANISM: Artificial Sequence
<220> FEATURE:
<223> OTHER INFORMATION: GFP sequence

<400> SEQUENCE: 5
atggagagcg acgagagcgg cctgcccgcc atggagatcg agtgccgcat caccggcacc 60
ctgaacggcg tggagttcga gctggtgggc ggcggagagg gcacccccaa gcagggccgc 120
atgaccaaca agatgaagag caccaaaggc gccctgacct tcagccccta cctgctgagc 180
cacgtgatgg gctacggctt ctaccacttc ggcacctacc ccagcggcta cgagaacccc 240
ttcctgcacg ccatcaacaa cggcggctac accaacaccc gcatcgagaa gtacgaggac 300
ggcggcgtgc tgcacgtgag cttcagctac cgctacgagg ccggccgcgt gatcggcgac 360
ttcaaggtgg tgggcaccgg cttccccgag gacagcgtga tcttcaccga caagatcatc 420
cgcagcaacg ccaccgtgga gcacctgcac cccatgggcg ataacgtgct ggtgggcagc 480
ttcgcccgca ccttcagcct gcgcgacggc ggctactaca gcttcgtggt ggacagccac 540
atgcacttca agagcgccat ccaccccagc atcctgcaga acgggggccc catgttcgcc 600
ttccgccgcg tggaggagct gcacagcaac accgagctgg gcatcgtgga gtaccagcac 660
gccttcaaga cccccattgc cttcgcc 687

<210> SEQ ID NO 6
<211> LENGTH: 11395
<212> TYPE: DNA
<213> ORGANISM: Artificial Sequence
<220> FEATURE:
<223> OTHER INFORMATION: synthetic FOLR-CAR DNA sequence

<400> SEQUENCE: 6
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840

-continued

```
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgatgagtaa ttcatacaaa aggactcgcc cctgccttgg   2220
ggaatcccag ggaccgtcgt taaactccca ctaacgtaga acccagagat cgctgcgttc   2280
ccgcccccctc acccgcccgc tctcgtcatc actgaggtgg agaagagcat gcgtgaggct   2340
ccggtgcccg tcagtgggca gagcgcacat cgcccacagt ccccgagaag ttggggggag   2400
gggtcggcaa ttgaaccggt gcctagagaa ggtggcgcgg ggtaaactgg gaaagtgatg   2460
tcgtgtactg gctccgcctt tttcccgagg gtgggggaga accgtatata agtgcagtag   2520
tcgccgtgaa cgttcttttt cgcaacgggt ttgccgccag aacacaggta agtgccgtgt   2580
gtggttcccg cgggcctggc ctctttacgg gttatggccc ttgcgtgcct tgaattactt   2640
ccacgcccct ggctgcagta cgtgattctt gatcccgagc ttcgggttgg aagtgggtgg   2700
gagagttcga ggccttgcgc ttaaggagcc ccttcgcctc gtgcttgagt tgaggcctgg   2760
cttgggcgct ggggccgccg cgtgcgaatc tggtggcacc ttcgcgcctg tctcgctgct   2820
ttcgataagt ctctagccat ttaaaatttt tgatgacctg ctgcgacgct ttttttctgg   2880
caagatagtc ttgtaaatgc gggccaagat ctgcacactg gtatttcggt ttttggggcc   2940
gcgggcggcg acggggcccg tgcgtcccag cgcacatgtt cggcgaggcg gggcctgcga   3000
gcgcggccac cgagaatcgg acgggggtag tctcaagctg gccggcctgc tctggtgcct   3060
ggcctcgcgc cgccgtgtat cgccccgccc tgggcggcaa ggctggcccg gtcggcacca   3120
gttgcgtgag cggaaagatg gccgcttccc ggccctgctg cagggagctc aaaatggagg   3180
acgcggcgct cgggagagcg ggcgggtgag tcacccacac aaaggaaaag ggcctttccg   3240
```

-continued

```
tcctcagccg tcgcttcatg tgactccacg gagtaccggg cgccgtccag gcacctcgat   3300
tagttctcga gcttttggag tacgtcgtct ttaggttggg gggaggggtt ttatgcgatg   3360
gagtttcccc acactgagtg ggtggagact gaagttaggc cagcttggca cttgatgtaa   3420
ttctccttgg aatttgccct ttttgagttt ggatcttggt tcattctcaa gcctcagaca   3480
gtggttcaaa gtttttttct tccatttcag gtgtcgtgat tcgaattcgc caccatggcc   3540
ctccctgtca ccgccctgct gcttccgctg gctcttctgc tccacgccgc tcggccccag   3600
ctggttgaat ctggcggagg actggtgcag cctggcagat ctctgagact gagctgtacc   3660
accagcggct tcaccttcgg cgactacgcc atgatttggg ccagacaggc ccctggcaaa   3720
ggcctggaat gggtgtccag catcagcagc agctccagct acatctacta cgccgacagc   3780
gtgaagggca gattcaccat cagccgggac aacgccaaga acagcctgta cctgcagatg   3840
aactccctga gagccgagga caccgccgtg tactattgcg ccagagagag atacgacttt   3900
tggagcggca tggacgtgtg gggcaagggc acaacagtga cagtctcttc tggcggcgga   3960
ggaagcggag gcggaggttc tggtggatct gcttggagtg ctctgacaca gcctgcctcc   4020
gtgtctggat ctcctggcca gagcatcaca atcagctgta ccggcaccag ctccgacgtg   4080
ggcagctaca atctggtgtc ctggtatcag caacaccccg gcaaggcccc taagctgatg   4140
atctacgagg gcagcaaaag acccagcggc gtgtccaata gattcagcgg cagcaagtct   4200
ggcaacgccg cctctctgac aatcagcgga ctgcaggctg aggacgaggc cgattactac   4260
tgccagagct acgacagcag cctgagcgtg gtgtttggcg gaggcaccaa actgacagtg   4320
ctgggaatcc ttgtgatctt ctctggaatg ttccttgttt tcaccctggc cggggccctg   4380
ttcctccatc aacgaaggaa atatagatca aacaaaggag aaagtcctgt ggagcctgca   4440
gagccttgtc attacagctg ccccagggag gaggagggca gcaccatccc catccaggag   4500
gattaccgaa aaccggagcc tgcctgctcc ccccgcgtga aattcagccg cagcgcagat   4560
gctccagcct acaagcaggg gcagaaccag ctctacaacg aactcaatct tggtcggaga   4620
gaggagtacg acgtgctgga caagcggaga ggacgggacc cagaaatggg cgggaagccg   4680
cgcagaaaga atccccaaga gggcctgtac aacgagctcc aaaaggataa gatggcagaa   4740
gcctatagcg agattggtat gaaaggggaa cgcagaagag gcaaaggcca cgacggactg   4800
taccagggac tcagcaccgc caccaaggac acctatgacg ctcttcacat gcaggccctg   4860
ccgcctcggg gatccgtcga cggcagtgga gagggcagag gaagtctgct aacatgcggt   4920
gacgtcgagg agaatcctgg cccaatggct atgatggagg tccagggggg acccagcctg   4980
ggacagacct gcgtgctgat cgtgatcttc acagtgctcc tgcagtctct ctgtgtggct   5040
gtaacttacg tgtactttac caacgagctg aagcagatgc aggacaagta ctccaaaagt   5100
ggcattgctt gtttcttaaa agaagatgac agttattggg accccaatga cgaagagagt   5160
atgaacagcc cctgctggca agtcaagtgg caactccgtc agctcgttag aaagatgatt   5220
ttgagaacct ctgaggaaac catttctaca gttcaagaaa agcaacaaaa tatttctccc   5280
ctagtgagag aaagaggtcc tcagagagta gcagctcaca taactgggac cagaggaaga   5340
agcaacacat tgtcttctcc aaactccaag aatgaaaagg ctctgggccg caaaataaac   5400
tcctgggaat catcaaggag tgggcattca ttcctgagca acttgcactt gaggaatggt   5460
gaactggtca tccatgaaaa agggttttac tacatctatt cccaaacata ctttcgattt   5520
caggaggaaa taaaagaaaa cacaaagaac gacaaacaaa tggtccaata tatttacaaa   5580
```

-continued

```
tacacaagtt atcctgaccc tatattgttg atgaaaagtg ctagaaatag ttgttggtct   5640
aaagatgcag aatatggact ctattccatc tatcaagggg gaatatttga gcttaaggaa   5700
aatgacagaa tttttgtttc tgtaacaaat gagcacttga tagacatgga ccatgaagcc   5760
agtttttttcg gggccttttt agttggccgc gaccatatga agcttggaag cggagctact   5820
aacttcagcc tgctgaagca ggctggagac gtggaggaga accctggacc tatggagagc   5880
gacgagagcg gcctgcccgc catggagatc gagtgccgca tcaccggcac cctgaacggc   5940
gtggagttcg agctggtggg cggcggagag ggcacccccca agcagggccg catgaccaac   6000
aagatgaaga gcaccaaagg cgccctgacc ttcagcccct acctgctgag ccacgtgatg   6060
ggctacggct tctaccactt cggcacctac cccagcggct acgagaaccc cttcctgcac   6120
gccatcaaca acggcggcta caccaacacc cgcatcgaga agtacgagga cggcggcgtg   6180
ctgcacgtga gcttcagcta ccgctacgag gccggccgcg tgatcggcga cttcaaggtg   6240
gtgggcaccg gcttccccga ggacagcgtg atcttcaccg acaagatcat ccgcagcaac   6300
gccaccgtgg agcacctgca ccccatgggc gataacgtgc tggtgggcag cttcgcccgc   6360
accttcagcc tgcgcgacgg cggctactac agcttcgtgg tggacagcca catgcacttc   6420
aagagcgcca tccaccccag catcctgcag aacgggggcc ccatgttcgc cttccgccgc   6480
gtggaggagc tgcacagcaa caccgagctg ggcatcgtgg agtaccagca cgccttcaag   6540
acccccattg ccttcgccag atcccgcgct cagtcgtcca attctgccgt ggacggcacc   6600
gccggacccg gctccaccgg atctcgcgtc gacggcagtg gagagggcag aggaagtctg   6660
ctaacatgcg gtgacgtcga ggagaatcct ggcccaatga ccgagtacaa gcccacggtg   6720
cgcctcgcca cccgcgacga cgtccccagg gccgtacgca ccctcgccgc cgcgttcgcc   6780
gactaccccg ccacgcgcca caccgtcgat ccggaccgcc acatcgagcg ggtcaccgag   6840
ctgcaagaac tcttcctcac gcgcgtcggg ctcgacatcg gcaaggtgtg ggtcgcggac   6900
gacggcgccg cggtggcggt ctggaccacg ccggagagcg tcgaagcggg ggcggtgttc   6960
gccgagatcg gcccgcgcat ggccgagttg agcggttccc ggctggccgc gcagcaacag   7020
atggaaggcc tcctggcgcc gcaccggccc aaggagcccg cgtggttcct ggccaccgtc   7080
ggcgtctcgc ccgaccacca gggcaagggt ctgggcagcg ccgtcgtgct ccccggagtg   7140
gaggcggccg agcgcgccgg ggtgcccgcc ttcctggaga cctccgcgcc ccgcaacctc   7200
cccttctacg agcggctcgg cttcaccgtc accgccgacg tcgaggtgcc cgaaggaccg   7260
cgcacctggt gcatgacccg caagcccggt gcctgatcta gaccgcgtct ggaacaatca   7320
acctctggat tacaaaattt gtgaaagatt gactggtatt cttaactatg ttgctccttt   7380
tacgctatgt ggatacgctg ctttaatgcc tttgtatcat gctattgctt cccgtatggc   7440
tttcattttc tcctccttgt ataaatcctg gttgctgtct ctttatgagg agttgtggcc   7500
cgttgtcagg caacgtggcg tggtgtgcac tgtgtttgct gacgcaaccc ccactggttg   7560
gggcattgcc accacctgtc agctcctttc cgggactttc gctttccccc tccctattgc   7620
cacggcggaa ctcatcgccg cctgccttgc ccgctgctgg acaggggctc ggctgttggg   7680
cactgacaat tccgtggtgt tgtcggggaa gctgacgtcc tttccatggc tgctcgcctg   7740
tgttgccacc tggattctgc gcgggacgtc cttctgctac gtcccttcgg ccctcaatcc   7800
agcggacctt ccttcccgcg gcctgctgcc ggctctgcgg cctcttccgc gtcttcgcct   7860
tcgccctcag acgagtcgga tctccctttg ggccgcctcc ccgcctggaa ttaattctgc   7920
agtcgagacc tagaaaaaca tggagcaatc acaagtagca atacagcagc taccaatgct   7980
```

```
gattgtgcct ggctagaagc acaagaggag gaggaggtgg gttttccagt cacacctcag   8040
gtacctttaa gaccaatgac ttacaaggca gctgtagatc ttagccactt tttaaaagaa   8100
aagaggggac tggaagggct aattcactcc caacgaagac aagatatcct tgatctgtgg   8160
atctaccaca cacaaggcta cttccctgat tagcagaact acacaccagg gccaggggtc   8220
agatatccac tgacctttgg atggtgctac aagctagtac cagttgagcc agataaggta   8280
gaagaggcca ataaaggaga gaacaccagc ttgttacacc ctgtgagcct gcatgggatg   8340
gatgacccgg agagagaagt gttagagtgg aggtttgaca gccgcctagc atttcatcac   8400
gtggcccgag agctgcatcc ggagtacttc aagaactgct gatatcgagc ttgctacaag   8460
ggactttccg ctggggactt tccagggagg cgtggcctgg gcgggactgg ggagtggcga   8520
gccctcagat cctgcatata agcagctgct ttttgcctgt actgggtctc tctggttaga   8580
ccagatctga gcctgggagc tctctggcta actagggaac ccactgctta agcctcaata   8640
aagcttgcct tgagtgcttc aagtagtgtg tgcccgtctg ttgtgtgact ctggtaacta   8700
gagatccctc agaccctttt agtcagtgtg gaaaatctct agcagtagta gttcatgtca   8760
tcttattatt cagtatttat aacttgcaaa gaaatgaata tcagagagtg agaggccttg   8820
acattgctag cgttttaccg tcgacctcta gctagagctt ggcgtaatca tggtcatagc   8880
tgtttcctgt gtgaaattgt tatccgctca caattccaca caacatacga gccggaagca   8940
taaagtgtaa agcctggggt gcctaatgag tgagctaact cacattaatt gcgttgcgct   9000
cactgcccgc tttccagtcg ggaaacctgt cgtgccagct gcattaatga atcggccaac   9060
gcgcggggag aggcggtttg cgtattgggc gctcttccgc ttcctcgctc actgactcgc   9120
tgcgctcggt cgttcggctg cggcgagcgg tatcagctca ctcaaaggcg gtaatacggt   9180
tatccacaga atcaggggat aacgcaggaa agaacatgtg agcaaaaggc cagcaaaagg   9240
ccaggaaccg taaaaaggcc gcgttgctgg cgtttttcca taggctccgc ccccctgacg   9300
agcatcacaa aaatcgacgc tcaagtcaga ggtggcgaaa cccgacagga ctataaagat   9360
accaggcgtt tccccctgga agctccctcg tgcgctctcc tgttccgacc ctgccgctta   9420
ccggatacct gtccgccttt ctcccttcgg gaagcgtggc gctttctcat agctcacgct   9480
gtaggtatct cagttcggtg taggtcgttc gctccaagct gggctgtgtg cacgaacccc   9540
ccgttcagcc cgaccgctgc gccttatccg gtaactatcg tcttgagtcc aacccggtaa   9600
gacacgactt atcgccactg gcagcagcca ctggtaacag gattagcaga gcgaggtatg   9660
taggcggtgc tacagagttc ttgaagtggt ggcctaacta cggctacact agaagaacag   9720
tatttggtat ctgcgctctg ctgaagccag ttaccttcgg aaaaagagtt ggtagctctt   9780
gatccggcaa acaaaccacc gctggtagcg gtggtttttt tgtttgcaag cagcagatta   9840
cgcgcagaaa aaaaggatct caagaagatc ctttgatctt ttctacgggg tctgacgctc   9900
agtggaacga aaactcacgt taagggattt tggtcatgag attatcaaaa aggatcttca   9960
cctagatcct tttaaattaa aaatgaagtt ttaaatcaat ctaaagtata tatgagtaaa  10020
cttggtctga cagttaccaa tgcttaatca gtgaggcacc tatctcagcg atctgtctat  10080
ttcgttcatc catagttgcc tgactccccg tcgtgtagat aactacgata cgggagggct  10140
taccatctgg ccccagtgct gcaatgatac cgcgagaccc acgctcaccg gctccagatt  10200
tatcagcaat aaaccagcca gccggaaggg ccgagcgcag aagtggtcct gcaactttat  10260
ccgcctccat ccagtctatt aattgttgcc gggaagctag agtaagtagt tcgccagtta  10320
```

-continued

```
atagtttgcg caacgttgtt gccattgcta caggcatcgt ggtgtcacgc tcgtcgtttg  10380

gtatggcttc attcagctcc ggttcccaac gatcaaggcg agttacatga tcccccatgt  10440

tgtgcaaaaa agcggttagc tccttcggtc ctccgatcgt tgtcagaagt aagttggccg  10500

cagtgttatc actcatggtt atggcagcac tgcataattc tcttactgtc atgccatccg  10560

taagatgctt ttctgtgact ggtgagtact caaccaagtc attctgagaa tagtgtatgc  10620

ggcgaccgag ttgctcttgc ccggcgtcaa tacgggataa taccgcgcca catagcagaa  10680

ctttaaaagt gctcatcatt ggaaaacgtt cttcggggcg aaaactctca aggatcttac  10740

cgctgttgag atccagttcg atgtaaccca ctcgtgcacc caactgatct tcagcatctt  10800

ttactttcac cagcgtttct gggtgagcaa aaacaggaag gcaaaatgcc gcaaaaaagg  10860

gaataagggc gacacggaaa tgttgaatac tcatactctt cctttttcaa tattattgaa  10920

gcatttatca gggttattgt ctcatgagcg gatacatatt tgaatgtatt tagaaaaata  10980

aacaaatagg ggttccgcgc acatttcccc gaaaagtgcc acctgacgtc gacggatcgg  11040

gagatcaact tgtttattgc agcttataat ggttacaaat aaagcaatag catcacaaat  11100

ttcacaaata aagcattttt ttcactgcat tctagttgtg gtttgtccaa actcatcaat  11160

gtatcttatc atgtctggat caactggata actcaagcta accaaaatca tcccaaactt  11220

cccaccccat accctattac cactgccaat tacctgtggt ttcatttact ctaaacctgt  11280

gattcctctg aattattttc attttaaaga aattgtattt gttaaatatg tactacaaac  11340

ttagtagttt ttaaagaaat tgtatttgtt aaatatgtac tacaaactta gtagt       11395
```